United States Patent
Schmidt-Jacobsen et al.

(10) Patent No.: US 8,021,440 B2
(45) Date of Patent: *Sep. 20, 2011

(54) METHOD FOR THE PREPARATION OF A CARMINIC ACID LAKE

(75) Inventors: Julie Faust Schmidt-Jacobsen, Rungsted (DK); Rikke Sakstrup Frandsen, Frederiksberg (DK)

(73) Assignee: CHR-Hansen A/S, Horsholm (DK)

( * ) Notice: Subject to any disclaimer, the term of this patent is extended or adjusted under 35 U.S.C. 154(b) by 0 days.

This patent is subject to a terminal disclaimer.

(21) Appl. No.: 12/621,769

(22) Filed: Nov. 19, 2009

(65) Prior Publication Data

US 2010/0061949 A1 Mar. 11, 2010

Related U.S. Application Data

(63) Continuation of application No. 11/577,751, filed as application No. PCT/EP2005/056195 on Nov. 24, 2005, now Pat. No. 7,641,704.

(30) Foreign Application Priority Data

Nov. 25, 2004 (EP) .................................... 04106069

(51) Int. Cl.
*D06P 1/00* (2006.01)
*C09B 61/00* (2006.01)
*A61K 35/64* (2006.01)

(52) U.S. Cl. ................................ 8/646; 8/636; 424/538

(58) Field of Classification Search .............. 8/646, 636; 424/63, 538; 435/41, 68.1
See application file for complete search history.

(56) References Cited

U.S. PATENT DOCUMENTS

2002/0058016 A1  5/2002 Ichi et al.
2003/0199019 A1*  10/2003 Ichi et al. ..................... 435/68.1

FOREIGN PATENT DOCUMENTS

EP         1 318 178 B1   11/2004
WO    WO 2006/056585      6/2006

OTHER PUBLICATIONS

M.T. Lizaso MD et al., "Identification of allergens involved in occupational asthma due to carmine dye", Annals of Allergy, Asthma, & Immunology, vol. 84, May 2000, pp. 549-552.
Non Final Office Action U.S. Appl. No. 11/577,751 dated May 12, 2009.
Notice of Allowance U.S. Appl. No. 11/577,751 dated Oct. 9, 2009.
EP Communication under Rule 71(3) EPC (EP Patent Application No. 04 106 069) dated Dec. 3, 2009.
EP Communication pursuant to Article 94(3) EPC (EP Patent Application No. 04 106 069) dated Jul. 10, 2009.
Applicants' Response to EP Communication pursuant to Article 94(3) EPC dated Jul. 10, 2009, response dated Jul. 29, 2009.

* cited by examiner

*Primary Examiner* — Lorna M Douyon
*Assistant Examiner* — Tanisha Diggs
(74) *Attorney, Agent, or Firm* — Stephen A. Bent; Foley & Lardner LLP

(57) ABSTRACT

A method for the preparation of carminic acid lakes, novel carminic acid lake compositions and their uses in foods, such as yogurt, fruit preparations, beverages, other miscellaneous food products that may need a stable red color, and in cosmetics.

4 Claims, No Drawings

METHOD FOR THE PREPARATION OF A CARMINIC ACID LAKE

CROSS-REFERENCE TO RELATED PATENT APPLICATIONS

This application is a Continuation application U.S. Ser. No. 11/577,751 filed Jun. 11, 2007, now U.S. Pat. No. 7,641,704, which is the U.S. National Phase of PCT/EP2005/056195 filed Nov. 24, 2005, which claims priority from European Patent Application No. 04106069.0 filed Nov. 25, 2004, which is incorporated herein by reference in it's entirety.

FIELD OF THE INVENTION

The present invention relates to a method for the preparation of carminic acid lakes, novel carminic acid lake compositions and their uses in foods, such as yogurt, fruit preparations, beverages, other miscellaneous food products that may need a stable red color, and in cosmetics.

BACKGROUND OF THE INVENTION

Carminic acid is a colorant, which can be extracted from the female insect bodies of *Dactylopius coccus costa* (alternative name *Coccus cacti* L.). The insects live on *Nopalea coccinellifera, Opuntia fidus indica* and other plants of the family Cactaceae cultivated for instance in the desert areas of Mexico and Central and South America. Depending on the pH the colorant may be a color in a spectrum from orange over red to purple and is generally known as cochineal or cochineal color. Carmine colorant is widely used in foods and beverages.

Carminic acid is harvested by extraction from the said insect's dried bodies with water or alcohol. During the aqueous based extraction of carminic acid from the insect, an amount of insect protein is also released from the insect and will be contained in the color extract. The level of insect protein is typically less than 0.5%. The aqueous based extract of cochineal is primarily containing carminic acid plus some cochineal protein and other minor extractable substances from the insect. Hereinafter this extract is referred to as cochineal extract solution.

It has been reported that the cochineal insect proteins could create some allergy related problems. In order to solve this allergy problem, US2002/0058016; EP1318178 (SAN-EI GEN (Japan)) describes a process wherein the cochineal extract solution is subjected to enzymatic proteolysis and *Dactylopius coccus costa* insect proteins with a molecular weight greater than 6,000 is subsequently removed.

The art describes numerous other not proteolysis based standard methods to make a pure carminic acid product substantially free of *Dactylopius coccus costa* insect proteins. Such methods generally use suitable adsorption treatments, ion exchange treatments, acid treatments and/or membrane treatments. Commercially available carminic acid products substantially free of *Dactylopius coccus costa* insect proteins include a water soluble Cochineal powder from Chr. Hansen, A/S (Denmark) or similar commercially available products from e.g. the companies Pronex (Peru) or Sensient.

A carminic acid lake denotes herein a type of coloring composition consisting essentially of carminic acid combined more or less definitely with aluminium and calcium. This is termed carminic acid calcium-aluminium lake. The lake is prepared by reacting carminic acid with aluminium and/or calcium under aqueous conditions. The conditions are adjusted in a way that favors precipitation of the aluminium/calcium-carminic acid lake complex composition. This complex composition is termed carmine.

The working example 2, US2002/0058016 (SAN-EI GEN (Japan)) describes preparation of a carminic acid calcium-aluminium lake based on a pure carminic acid solution made in example 1. Example 2 section [0085] then explains that "when a carminic acid aluminium lake or calcium lake (Carmine) is caused to form a polymer, there is the tendency that when a low molecular protein is allowed to be present, a more neat lake can be obtained with an increased intensity of red color. Therefore, a cochineal color (carmine) with a higher intensity of redness and an increase market value may be prepared by adding a protein of comparatively low molecular weight, which does not become an allergen to the above allergen-free solution." Besides this speculative statement, no further relevant details with respect to a possible addition of low molecular weight protein to the carminic acid lake are described.

SUMMARY OF THE INVENTION

The aim of the present invention is to provide an improved carminic acid lake, which is free of potentially allergenic cochineal insect proteins.

The solution is based on several relevant parameters important for the preparation of an optimal lake which have been identified by the present inventors by starting from a pure carminic acid product substantially free of *Dactylopius coccus costa* insect proteins. These parameters are described in further details below and include details regarding added non cochineal insect proteins and carminic acid percentage.

Accordingly, a first aspect of the invention relates to a process for making a carminic acid lake comprising the steps of:
(i) treating an aqueous solution,
   comprising
    (a) 0.5 to 15% (g/l) carminic acid and
    (b) from 0.75 to 15% (g/l) not *Dactylopius coccus costa* insect proteins, where substantially all of the not *Dactylopius coccus costa* insect proteins have a molecular weight (MW) below 10,000 Da,
   wherein the aqueous solution is substantially free of *Dactylopius coccus costa* insect proteins with a molecular weight (MW) above 6,000 Da;
   with an aluminium and calcium compound,
(ii) adjusting the conditions to get suitable conditions to produce a calcium-aluminium carminic acid lake, wherein the lake comprises
    (a) from 40 to 80% carminic acid (dry weight) and
    (b) from 10 to 30% not *Dactylopius coccus costa* insect proteins (dry weight), where substantially all of the not *Dactylopius coccus costa* insect proteins have a molecular weight (MW) below 10,000 Da and
   wherein the lake is substantially free of *Dactylopius coccus costa* insect proteins with a molecular weight (MW) above 6,000 Da.

A commercially produced cochineal extract solution normally comprises around 0.6% carminic acid and relatively low amounts *Dactylopius coccus costa* insect proteins, generally around 0.1 to 0.25% of proteins. In the art this has been regarded as a sufficient amount of proteins to produce a lake. Contrary to the art, the present inventors identified that improved lakes may be obtained by including higher amounts of proteins as described herein. An advantage of using significantly higher amounts of proteins, as described in step (i) above, is that the yield of carminic acid is improved. The yield relates to the amount of carminic acid in the lake of step (ii) as compared to the initial amount in the aqueous solution of step (i). See working examples herein for further details, where yields up to 98.2% have been obtained.

At the filing date of the present application, the present inventors were not aware of any prior art (for instance commercial lake products) that describes carminic acid lake with the amounts of carminic acid and non insect proteins as described herein.

Accordingly, a second aspect relates to a carminic acid calcium-aluminium lake obtainable by a process of the first aspect and embodiments thereof as described herein, wherein the lake comprises
  (a) from 40 to 80% of carminic acid (dry weight) and
  (b) from 10 to 30% of not *Dactylopius coccus costa* insect proteins (dry weight), where substantially all of the not *Dactylopius coccus costa* insect proteins have a molecular weight (MW) below 10,000 Da and
  wherein the lake is substantially free of *Dactylopius coccus costa* insect proteins with a molecular weight (MW) above 6,000 Da.

The word "obtainable" shall be understood in the normal English sense of the word, i.e. as the lake may be obtained by the specified process but could in theory be obtained in a different manner. Preferably, the lake of the second aspect is obtained by a process of the first aspect and embodiments thereof as described herein.

A third aspect of the invention relates to use of a carminic acid aluminium lake, a carminic acid calcium lake or a carminic acid calcium-aluminium lake of the second aspect and embodiments thereof as described herein for making a color composition to be added to food products, sweets, confectionary, beverages, pharmaceuticals or cosmetics.

This third aspect may alternatively be described as a method for colouring food products, sweets, confectionary, beverages, pharmaceuticals or cosmetics comprising use of a color composition made from a carminic acid aluminium lake, a carminic acid calcium lake or a carminic acid calcium-aluminium lake of the second aspect and embodiments thereof as described herein.

DETAILED DESCRIPTION OF THE INVENTION

A Process for Making a Carminic Acid Lake

The carminic acid to be used to make the aqueous solution of step (i) shall preferably be from a pure carminic acid composition. A "pure carminic acid composition" denotes herein a highly purified cochineal extract solution. Preferably it comprises from 90 to 99% carminic acid (dry weight) and is preferably substantially free of *Dactylopius coccus costa* insect proteins.

The term "substantially free of *Dactylopius coccus costa* insect proteins" denotes herein that it is not detectable by a SDS-PAGE analysis. A suitable SDS-PAGE analysis is given in Example 1.

A pure carminic acid composition may be made in a number of routine ways e.g. based on methods that generally use suitable adsorption treatments, ion exchange treatments, acid treatments and/or membrane treatments. Commercially available pure carminic acid compositions include a water soluble Cochineal powder from Chr. Hansen, A/S (Denmark) or similar commercially available products from e.g. the companies Pronex (Peru) or Sensient. A pure carminic acid composition may be made by the proteolysis based method described in US2002/0058016.

The not *Dactylopius coccus costa* insect proteins used to make the aqueous solution of step (i) shall preferably be from a protein composition obtained from a source that is acceptable for the food industry and/or pharmaceutically acceptable. For example, the proteins should preferably not be based on a composition of proteins obtained from e.g. a snake known to be toxic for e.g. humans. It should furthermore preferably be from a source known to cause no or only acceptable allergy related problems.

The term "not *Dactylopius coccus costa* insect proteins" used to make the aqueous solution of step (i) globally denotes herein peptides, amino acids, proteins or mixtures thereof.

Examples of suitable protein compositions are based on plant proteins such as soya proteins and potato proteins.

Preferably, the proteins are milk proteins such a cow milk proteins. Preferably, the milk proteins are obtained from a milk-based hydrolysate such as a whey hydrolysate. Suitable commercially available whey hydrolysate may be obtained from commercial dairy companies. This is particularly relevant when the carminic acid color is to be used in a milk based food product.

Preferably, substantially all of the not *Dactylopius coccus costa* insect proteins have a molecular weight (MW) below 6,000 Da, more preferably below 4,000 Da and even more preferably below 3,000 Da.

It is implicit in the process as described herein that when the proteins of step (i) have a certain MW then the resulting lake of step (ii) will also get a corresponding protein MW composition. For instance, if substantially all of the proteins of step (i) have a molecular weight (MW) below 6,000 Da then substantially all of the proteins in the lake, of step (ii) will have a molecular weight (MW) below 6,000 Da.

The term "substantially all of the proteins have a molecular weight (MW) below [a number] Da" denotes herein that proteins with a greater MW than indicated are not detectable by a SDS-PAGE analysis. A suitable SDS-PAGE analysis is given in Example 1.

An aqueous solution may preferably be prepared simply by adding a suitable protein composition (e.g. in powder form) to a pure carminic acid solution or simply by adding e.g. pure carminic acid (e.g. in powder form) to a solution comprising a suitable protein composition. In other words, simply by mixing a suitable protein composition with a suitable pure carminic acid composition.

In the aqueous solution of step (i) of the first aspect it is preferred that the ratio Carminic acid/not *Dactylopius coccus costa* insect proteins (g/l) is less than 1. The present inventors have identified that if the ratio is greater than 1 the solution has a tendency to gel. See table of working example 1 herein.

Preferably, the ratio Carminic acid/not *Dactylopius coccus costa* insect proteins (g/l) is from 0.4 to 0.9, more preferably from 0.5 to 0.8 and most preferably from 0.5 to 0.7.

Before the proteins are added to the aqueous solution, the pH of the solution shall preferably be adjusted to a pH from 5 to 7, more preferably around pH 6.

Preferably, the aqueous media is water, preferably distilled water.

Preferably, the aqueous solution is substantially free of *Dactylopius coccus costa* insect proteins.

Preferably, the aqueous solution comprises from 1 to 10% carminic acid and from 1.5 to 10% not *Dactylopius coccus costa* insect proteins, more preferably the aqueous solution comprises from 2 to 7% carminic acid and from 3 to 8% not *Dactylopius coccus costa* insect proteins, even more preferably the aqueous solution comprises from 3 to 5% carminic acid and from 4 to 6% not *Dactylopius coccus costa* insect proteins.

The carminic acid/protein aqueous solution is treated with the aluminium and calcium compound under suitable conditions to produce the carminic acid lake. The skilled person generally knows suitable conditions to make a lake. However, the present inventors have analyzed this in detail and the preferred conditions are explained below.

Treatment of the aqueous solution with an aluminium and calcium compound may be performed in different ways. It may e.g. be performed by adding the aluminium and calcium to a solution only comprising the proteins and then thereafter by adding the carminic acids to the solution.

However, it is preferred to first make an aqueous solution comprising both the carminic acid and the proteins and then add the aluminium and calcium compound to this solution.

Without being limited by theory, it is believed to be important for optimal lake formation that the aluminium and calcium are added to a solution already comprising both the carminic acid and the proteins.

In fact this is different to the suggestion in working example 2 of US2002/0058016, where a carminic acid aluminium solution is first made and it is then suggested to add low MW proteins to this solution.

It is preferred to first add the aluminium and then wait for a suitable time before the calcium is added to the aqueous solution. A suitable time is around from 30 seconds to 1 hour, preferably from 1 minute to 15 minutes.

Surprisingly, the present inventors have identified that if calcium is added to the carminic acid/protein solution first, then there is a risk of unwanted "black spots" developing in the final lake. The black spots are believed to be calcium carminate. There are created far less "black spots" when aluminium is added first to the carminic acid/protein aqueous solution. See working example 2 herein for further details.

Preferably, the aqueous solution is treated with from 1 g aluminium/l solution to 20 g aluminium/l solution and from 1 g calcium/l solution to 20 g calcium/l solution.

The skilled person knows how to optimize this in relation to the desired color of interest.

A suitable aluminium compound is aluminium sulphate. Preferably the aluminium compound is $AlK(SO_4)_2 * 12H_2O$. A suitable calcium compound is calcium carbonate or Calcium chloride. Preferably the calcium compound is $(CH3COO)_2Ca*H_2O$.

During the treatment of the carminic acid/protein aqueous solution with the aluminium and/or calcium compound it is preferred to adjust the pH to a value from 3 to 7 in order to produce the carminic acid lake. Preferably, the pH is adjusted to a value from 4 to 6 and more preferably adjusted to a pH value from 4.5 to 5.5.

The adjustment of the pH may be done after the carminic acid/proteins has been combined with the salts. However, preferably the adjustment is done before addition of salts.

Preferably the carminic acid/protein aqueous solution is treated with the aluminium and calcium compound under following suitable conditions to produce the carminic acid lake:
  time period: 15 minutes to 2 hours, more preferably from 30 minutes to 60 minutes
  temperature: from 80° C. to 99° C., more preferably from 92° C. to 97° C.

The final composition of the produced carminic acid lake of step (ii) relates to the initial composition of the aqueous solution of step (i). The preferred carminic acid/protein contents of the aqueous solution are given above. Corresponding preferred compositions of the produced carminic acid lake of step (ii) are wherein the lake comprises from 55 to 75% carminic acid (dry weight) and from 15 to 25% proteins (dry weight), more preferably wherein the lake comprises from 62 to 72% carminic acid (dry weight) and from 18 to 22% proteins (dry weight).

Of course the amount of carminic acid and proteins in the lake cannot be more than 100%. Actually, the sum will generally be around 90% since the lake will comprise other material such as the salts used to produce the lake. Accordingly, if the lake comprises 75% carminic acid (dry weight) then it would normally not have more than 15% proteins (dry weight).

A preferred method to determine the amounts of carminic acid is a known standard method described by FAO/WHO: Document from $44^{th}$ session of the JECFA committee in 1995 and Food Chemical Codex, second edition (FCCII). In Commission Directive 94/45/EC from July 1995, Official journal of the European Communities No. L 226, p. 9, it is described that the proper diluted color product E-120 has a maximum at 494 nm.

A preferred method to determine the amount of proteins is the known Kjeldahl method and/or by amino acid analysis.

After the carminic acid lake of step (ii) is produced it is routine to include adequate subsequent steps. These may include a step of filtering the carminic acid lake and/or a step of drying the carminic acid lake to get a dried carminic acid lake. These steps are routine for the skilled persons and reference is made to the reference textbook given above.

Use of a Carminic Acid Lake in Different Products

In order to use the carminic acid lake, as described herein, it should be converted into a suitable color composition. The term color composition should be understood broadly. Depending on the final needs it may be the carminic acid lake as such or maybe the lake after filtering and/or drying. Alternatively, the lake may be converted into a suitable carmine solution or water-soluble carmine (powder).

However, it may also be a color composition where a suitable carrier or additive which is food sanitation-wise or pharmaceutically acceptable has been added. The specific choice of carrier or additive will depend on the final use, e.g. in food or pharmaceuticals, and the skilled person may routinely select adequate carriers or additives. For further details, see US2002/0058016.

As said above, the color composition may be added to food products, sweets, confectionary, beverages, pharmaceuticals or cosmetics.

The term food product denotes herein both food and feed products. Preferably it is food products. Preferred food products include dairy products such as yogurt or meat.

A further relevant feature of the color composition is the strength of the color. The color of the carminic acid may e.g. be red and the color composition may be made with different strength of e.g. red in order to get an adequate color in the final e.g. food product.

Starting from the carminic acid lake, as described herein, it is routine work to make adequate steps to get a color composition with required color strength.

The color composition may be encapsulated, using conventional microencapsulation techniques suitable for food products, for example, as described in WO97/26803 (Chr. Hansen A/S), by encapsulation in gum arabic.

EXAMPLES

Materials and Analytical Methods

Pure carminic acid: Commercially available carminic Acid obtained from purified cochineal extract (*Dactylopius coccus Costa*). Minimum around 90% Carminic Acid.

Protein composition: Commercial whey protein hydrolysate suitable as protein source in infant formulas with reduced allergen content. Substantially all of the proteins have a molecular weight (MW) below 6,000 Da.

ELISA analysis: Antigenecity tested by one site immunometic assay ELISA with polyclonal antibodies raised on whey protein concentrate μg protein eqv./g protein max 85

Aluminium salt: $AlK(SO_4)_2*12H_2O$

Calcium salt: $(CH_3COO)_2Ca*H_2O$

Acetic Acid: $CH_3COOH$

Sodium Hydroxide: NaOH-pellets

SDS-PAGE Analysis

Solvent Tris buffer pH 8 (20 g Tris/1,000 ml demi water, pH adjusted with conc. HCl)

The lakes of carmine were added buffer solution so that all samples contained the same amount Carminic Acid/ml corresponding to 1.5 g/l of a 46.56% C.A. lake.

Marker 12 or Sea Blue is applied as the protein size indicator (MW)

1M DL-Dithiothreitol (DTT): 20 mg DTT solution in 130 μl MQW

Volume added to the gel: Mark 12 5 μl, Sea Blue 7 μl, Carmine samples 10 μl NUPAGE Novex high performance pre-cast gel 4-12% BIS-TRIS are stained by cromassie blue and/or silver Example 1

Production of Carminic Acid Lake

This example discloses examples of preparation of Al—Ca carmine lake with carminic acid and whey hydrolysate.

An amount of 21 g Carminic acid was dissolved in 500 ml water and in this carmine solution 33 g peptide was dissolved. pH was adjusted to 5 and the temperature was raised to 85-95° C. Then 8 g $AlK(SO_4)_2*12H_2O$ was dissolved in 50 ml water and added to the solution and then 8.2 g $(CH_3COO)_2Ca*H_2O$ was dissolved in 50 ml water and added to the solution. After 45 minutes 70-98% of the carminic acid in the solution was converted to carmine lake, which precipitated from the solution. The carmine lake was separated from the solution, dried and analyzed.

| % C.A. | % Protein | C.A./Protein | % Al salt | % Ca salt | % Yield | Processing |
|---|---|---|---|---|---|---|
| 4.5 | 1.5 | 2.61 | 1.6 | 1.6 | — | Impossible |
| 4.5 | 2.2 | 1.78 | 1.6 | 1.6 | — | Impossible |
| 2.5 | 1.0 | 2.17 | 1.6 | 1.6 | — | Impossible |
| 3.25 | 5 | 0.7 | 1.6 | 1.6 | 98.4 | Easy |
| 2 | 3 | 0.7 | 0.9 | 0.8 | 93.9 | Easy |
| 0.75 | 1 | 0.8 | 0.24 | 0.25 | 85.2 | Easy |
| 4 | 6.7 | 0.6 | 1.6 | 1.6 | 98.2 | Easy |
| 4 | 5.7 | 0.7 | 1.6 | 1.6 | 97.7 | Easy |
| 4 | 5.0 | 0.8 | 1.6 | 1.6 | 97.4 | Easy |
| 4 | 4.4 | 0.9 | 1.6 | 1.6 | 95.0 | Possible |

The resulting carmine lakes had a carminic acid content of 65-75% and a protein content of 18-22%. None of the proteins in the lakes, detectable in the SDS-PAGE analysis, were bigger than 3,000 Da.

The resulting carmine lakes have bright red color shades and were applicable as cochineal protein based carmine lakes for making carmine solutions and water soluble carmine powders.

Conclusions:

The results shown in the table in example 1 demonstrates the following:

(1) that optimal carminic acid yields are obtained when the aqueous solution comprises from 3% to 5% carminic acid and from 4% to 7% of whey protein hydrolysate;

(2) when the amount of protein is increased, within the ranges as described herein, the yield is improved;

(3) that the ratio carminic acid/added proteins shall be less than 1 to avoid gelling and thereby impossible processing. Furthermore, the preferred ratio is from 0.5 to 0.8 and most preferably around 0.6.

Example 2

This example discloses examples of Al—Ca carmine lake preparation with carminic acid and whey hydrolysate.

An amount of 21 g Carminic acid was dissolved in 500 ml water and in this carmine solution 33 g peptide was dissolved. pH was adjusted to 5 and the temperature was raised to 85-95° C. Then 8 g $(CH_3COO)_2Ca*H_2O$ was dissolved in 50 ml water and added to the solution and then 8.2 g $AlK(SO_4)_2*12H_2O$ was dissolved in 50 ml water and added to the solution. After 45 minutes 70-98% of the carminic acid in the solution had been converted to carmine lake, which precipitated from the solution. The carmine lake was separated from the solution, dried and analyzed.

Visible black spots in the lake were identified. The black spots were most likely calcium carminate, which had not undergone the change from calcium carminate to aluminium-calcium carmine lake.

By adding the $AlK(SO_4)_2*12H_2O$ solution first, it is believed, that the aluminium and peptide attach to the carminic acid and makes it difficult/impossible for the calcium to form calcium carminate before it forms aluminium-calcium carmine lake.

Conclusions:

The result in example 2 demonstrates that it is important to first add the aluminium, wait for a period and then add the calcium in order to get less "black spots".

The invention claimed is:

1. A process for making a carminic acid lake, comprising treating an aqueous solution with an aluminium and calcium compound, said aqueous solution comprising
   from 0.5% to 15% of carminic acid and
   from 0.75% to 15% of protein, said protein being other than a *Dactylopius coccus costa* insect protein,
   under conditions such that a carminic acid lake is produced that comprises
   from 40% to 80% by dry weight of carminic acid and
   from 10% to 30% by dry weight of said protein,
   wherein (i) substantially all of said protein has a molecular weight below 10,000 Da, (ii) said aqueous solution is substantially free of *Dactylopius coccus costa* insect proteins with a molecular weight above 6,000 Da, and (iii) the ratio of said carminic acid to said protein in said aqueous solution is less than 1.

2. The process of claim 1 wherein, said ratio is from about 0.5 to about 0.8.

3. The process of claim 1 wherein, said ratio is from about 0.5 to about 0.7.

4. The process of claim 1, wherein the aluminum compound is added first and then the calcium compound is added to the aqueous solution.

* * * * *